US012773545B2

(12) United States Patent
Oda et al.

(10) Patent No.: US 12,773,545 B2
(45) Date of Patent: Oct. 27, 2026

(54) NEEDLELESS CONNECTOR HAVING CHECK VALVE WITH ASYMMETRIC VALVE DESIGN AND PRIMARY SEAL SUPPORT

(71) Applicant: CareFusion 303, Inc., San Diego, CA (US)

(72) Inventors: Todd Oda, Torrance, CA (US); George Mansour, Diamond Bar, CA (US); Tomas Frausto, Walnut, CA (US); Ali Saleh, Irvine, CA (US); Archana Rao, Los Angeles, CA (US); Siddarth Shevgoor, Mission Viejo, CA (US)

(73) Assignee: CAREFUSION 303, INC., San Diego, CA (US)

( * ) Notice: Subject to any disclaimer, the term of this patent is extended or adjusted under 35 U.S.C. 154(b) by 974 days.

(21) Appl. No.: 17/307,624

(22) Filed: May 4, 2021

(65) Prior Publication Data

US 2022/0355092 A1 Nov. 10, 2022

(51) Int. Cl.
*A61M 39/22* (2006.01)
*A61M 39/26* (2006.01)

(52) U.S. Cl.
CPC ....... *A61M 39/22* (2013.01); *A61M 2039/267* (2013.01)

(58) Field of Classification Search
CPC ............ A61M 39/22; A61M 2039/267; A61M 39/26; A61M 2039/263; A61M 2039/266; A61M 2039/2433; A61M 39/225
See application file for complete search history.

(56) References Cited

U.S. PATENT DOCUMENTS 6,855,138 B2 * 2/2005 Tsai ...................... A61M 39/26 604/537
10,463,796 B2 * 11/2019 Thorne ............... A61M 5/3129
(Continued)

FOREIGN PATENT DOCUMENTS

| | | | |
|---|---|---|---|
| CN | 107626037 | A | 1/2018 |
| JP | 2015505485 | A | 2/2015 |
| JP | 2015533613 | A | 11/2015 |

OTHER PUBLICATIONS

International Search Report and Written Opinion for Application No. PCT/US2022/026044, dated Jul. 27, 2022, 13 pages.
(Continued)

*Primary Examiner* — Courtney Fredrickson
(74) *Attorney, Agent, or Firm* — MASCHOFF BRENNAN

(57) ABSTRACT

A needleless connector may include a housing comprising a central longitudinal axis, a body portion, and a base portion. The body portion may include an inner surface forming an internal cavity, and a first port forming a first fluid passage to the internal cavity. The base portion may include a top section including a valve seal support, and a bottom section including a second port forming a second fluid passage to the internal cavity. The needleless connector may further include an asymmetrically-shaped valve disposed in the internal cavity. The asymmetrically-shaped valve may include a head portion, a valve body portion extending distally from the head portion, and a wall having an inner surface forming a valve cavity. The valve may be coupled with the housing such that the inner surface of the valve at the valve body portion is seated and radially supported on the valve seal support.

17 Claims, 1 Drawing Sheet

(56) References Cited

U.S. PATENT DOCUMENTS

| | | | | |
|---|---|---|---|---|
| 2009/0292274 | A1* | 11/2009 | Guala | A61M 39/045<br>604/533 |
| 2013/0193359 | A1* | 8/2013 | Yeh | A61M 39/26<br>251/149.1 |
| 2014/0135709 | A1* | 5/2014 | Zollinger | A61M 39/20<br>604/246 |
| 2014/0276463 | A1* | 9/2014 | Mansour | A61M 39/10<br>604/256 |
| 2017/0290216 | A1* | 10/2017 | Truitt | A61M 39/0208 |

OTHER PUBLICATIONS

Australian Office Action for Application No. 2022268862, dated Jun. 25, 2025, 3 pages.
Extended European Search Report for Application No. 26156242.5, dated Feb. 17, 2026, 9 pages.
Japanese Office Action for Application No. 2023-562240, dated Dec. 4, 2025, 7 pages.
Indian Office Action for Application No. 202317065141, dated Aug. 19, 2026, 7 pages.
Japanese Office Action for Application No. 2023-562240, dated Jun. 24, 2026, 5 pages including translation.

* cited by examiner

NEEDLELESS CONNECTOR HAVING CHECK VALVE WITH ASYMMETRIC VALVE DESIGN AND PRIMARY SEAL SUPPORT

TECHNICAL FIELD

The present disclosure relates generally to needleless connectors, and, in particular, to needleless connectors with a valve member having asymmetric valve geometry with a long valve stem and a primary seal that is located close to the base side of the connector.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

Due to the nature of currently existing and/or prior art needleless valve geometries, fluid is commonly deposited on the face of the valve head upon removal of a medical implement (e.g., a mating male luer or a syringe) used to apply an axial force to place the valve member in an open position. In these currently existing needleless valves, fluid deposited on the valve head will occasionally separate from the valve member and flow into the fluid path for administering to a patient, thereby causing anxiety along with potential blood stream diseases.

The description provided in the background section should not be assumed to be prior art merely because it is mentioned in or associated with the background section. The background section may include information that describes one or more aspects of the subject technology.

SUMMARY

According to various embodiments of the present disclosure, a needleless connector may include a housing comprising a central longitudinal axis, a body portion, and a base portion. The body portion may include an inner surface forming an internal cavity, and a first port forming a first fluid passage to the internal cavity. The base portion may include a top section including a valve seal support, and a bottom section including a second port forming a second fluid passage to the internal cavity. The needleless connector may further include an asymmetrically-shaped valve disposed in the internal cavity. The asymmetrically-shaped valve may include a head portion, a valve body portion extending distally from the head portion, and a wall having an inner surface forming a valve cavity. The valve may be coupled with the housing such that the inner surface of the valve at the valve body portion is seated and radially supported on the valve seal support.

According to various embodiments of the present disclosure, a needleless connector may include a housing comprising a central longitudinal axis, a body portion including an inner surface forming an internal cavity, and a base portion, and an asymmetrically-shaped valve disposed in the internal cavity. The body portion may further include a first port forming a first fluid passage to the internal cavity. The base portion may have a top section including a valve seal support, and a bottom section including a second port forming a second fluid passage to the internal cavity. The asymmetrically-shaped valve may include an elongate head portion, a body portion extending distally from the elongate head portion, and a wall having an inner surface forming a valve cavity. The wall may define a radially-inward extending ledge, and the top section may further include a radially-outward extending ledge which abuts the radially-inward extending ledge of the valve to prevent the valve from being displaced into the first port.

According to various embodiments of the present disclosure, a needleless connector may include a housing comprising a central longitudinal axis, a body portion including an inner surface defining an internal cavity, and a base portion, and an asymmetrically-shaped valve disposed in the internal cavity. The body portion may include a first port forming a first fluid passage to the internal cavity, and a bottom section including a second port forming a second fluid passage to the internal cavity. The asymmetrically-shaped valve may include an elongate head portion, a body portion extending distally from the elongate head portion, and a wall having an inner surface forming a valve cavity. An outer surface of the valve may include a primary seal portion and a secondary seal portion spaced apart from the primary seal portion. The primary seal portion may be located adjacent the base portion of the housing such that a distance between the primary seal portion and the base portion is smaller than a distance between the secondary seal portion and the primary seal portion.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following FIGURES are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1B:
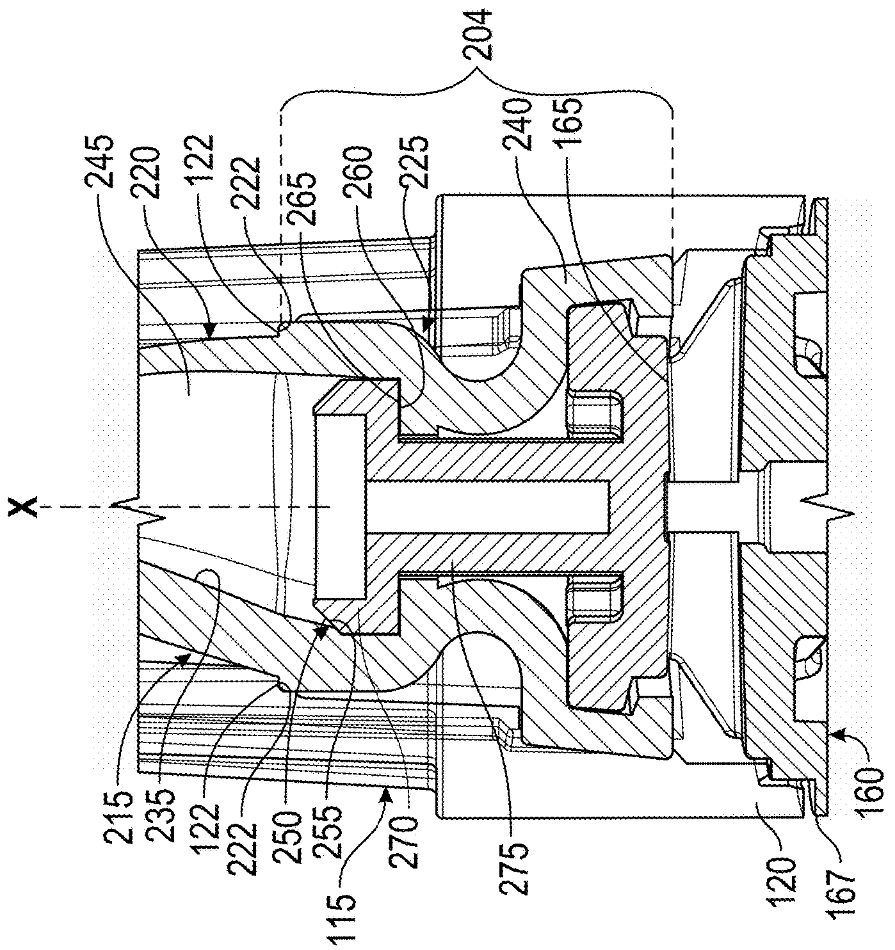
FIG. 1B is an enlarged partial cross-sectional view of the needleless connector of FIG. 1A, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are generally directed to a self-sealing, needleless connector that incorporates a resilient, compressible valve disposed within a housing of the connector, in which the compressible valve has an asymmetric valve geometry with a long valve stem and a primary seal that is located close to the base side of the connector. The long valve stem and asymmetric valve geometry allow the valve to be activated and retracted in a more controlled manner. This prevents fluid from exiting (splashing off) the connector upon a rapid syringe disconnect.

As described herein, and as shall be appreciated, locating the primary seal of the valve close to the base of the connector housing creates a more robust seal. Advantageously, the preload on the valve remains more consistent with varying manufacturing tolerances of the connector. In contrast in currently existing connectors in which the valve has a primary seal located far from the base, the seal may lose preload on the seal due to buckling of the thin-walled valve over a long distance. For the same reason, the valve preload/sealing ability is sensitive to manufacturing tolerances.

Accordingly, the needleless connectors of the various embodiments described herein present several advantages over currently existing needleless connectors. For example, due to the design of the long neck asymmetric valve geometry, the valve may activate and retract in a far more controlled manner than the valve in currently existing needleless connectors. In contrast, the currently existing needleless connectors present several challenges. For example, since the top half of the valve is solid silicone, the valve has a very high spring rate. As the valve of the currently existing needleless connectors is retracted quickly (such as during pulling off the syringe rapidly), the solid silicone portion of the valve tends to unwind and spring back violently. This may disadvantageously cause fluid to splash out of the currently existing connector. Additionally, the valve of the currently existing needleless connectors is very sensitive to manufacturing variances. Since the primary seal of the currently existing valve is supported by a long column of thin-walled silicone, the loss of preload on the valve becomes more pronounced with slight tolerance changes of the components or the assembly of the connector itself. Further, because the strength of the currently existing valve is dictated by the silicone, under high back pressures, the currently existing valve has a tendency to bulge out of the access port of the currently existing connector.

In some embodiments, the base of the connector housing may be designed to support the primary seal of the valve in several ways. For example, in some embodiments at least a portion of the base may be designed to provide a radial support to the valve in the primary seal area. This radial support may advantageously prevent the valve from being "crushed in" or otherwise similarly deformed with high back pressures. In some embodiments, at least a portion of the base of the connector may be designed to "hold" the valve and prevent the valve from bulging out of the access port with high back pressures.

While the following description is directed to the administration of medical fluid to a patient by a medical practitioner using the disclosed needleless connector, it is to be understood that this description is only an example of usage and does not limit the scope of the claims.

Figure 1A:
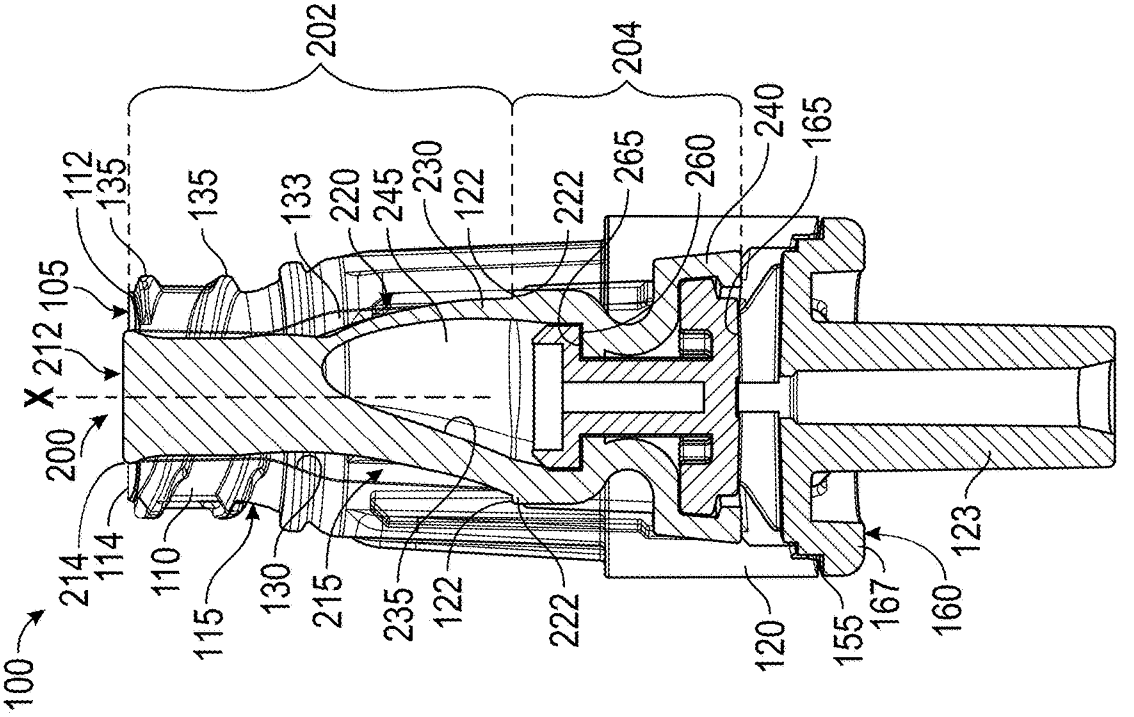
FIG. 1A illustrates a housing of a needleless connector having a compressible valve installed therein, in accordance with some embodiments of the present disclosure.

FIG. 1A illustrates a housing 110 of a needleless connector 100 having a compressible valve 200 installed therein, in accordance with some embodiments of the present disclosure. FIG. 1B is an enlarged partial cross-sectional view of the needleless connector 100 of FIG. 1A, in accordance with some embodiments of the present disclosure. As depicted, the housing 110 may have a proximal end 105 defining an inlet port 112 of the housing 110, a distal end 120 including a base portion 160 defining an outlet port 123 of the housing 110, and a central longitudinal axis X extending through the proximal and distal ends 105 and 120, In some embodiments, the housing 110 may further include an inner surface 130 defining an internal cavity 133 that extends at least partially between the proximal and distal ends 105 and 120 of the housing 110. The housing 110 may be formed of a body portion 115 coupled to or otherwise integrally formed with the base portion 160. However, in some embodiments, the housing 110 may be formed from a combination of other pieces or parts similarly dimensioned to house the compressible valve 200 therein. In operation, a fluid pathway may be established through needleless connector 100 from the inlet port 112 to the outlet port 123, for example. As referred to herein, proximal refers to an orientation toward the inlet port 112 of the housing 110, and distal refers to an orientation toward the base portion 160 or bottom of the housing 100, opposite the inlet port 112.

As depicted, in addition to housing 110 including the inlet port 112 of the housing 110 for interfacing with a medical implement, for example, a syringe, the housing 110 may further include an opening 155 for connecting with the base portion 160 of the housing 110. The lower section of the body portion 115 (e.g., a section proximal to the opening 155) may have an increased diameter and include one or more internal contact tabs (not shown). When assembled in a needleless connector 100, the one or more internal contact tabs may provide a radial force substantially orthogonal to the central longitudinal axis X of the housing 110 onto a flange portion 240 of the compressible valve 200 that is arranged on a valve mount of the base portion 160.

In accordance with various embodiments of the present disclosure, the inlet port 112 may include a top port surface 114 and a channel defined in the internal cavity 133. The inlet port 112 may include engagement features 135 for coupling to another device (e.g., a fluid transfer assembly). For example, engagement features 135 may include cooperating mechanical elements, such as internal or external surface threads, detents, bayonet-type locking elements, etc., as well as other surface configurations, such as a tapered Luer surface for frictional engagement. In some embodiments, the inlet port 112 may define a female luer fitting with luer lock threading 135. The inner surface 130 and the internal cavity 133 defined therein may extend longitudinally from the opening of the top port surface 114 of the inlet port 112 into the internal cavity 215 of the body portion 115 of housing 110.

In some embodiments, an internal sealing edge 122 may be defined on the inner surface 130 of the housing 110. The internal sealing edge 122 may be a circumferential edge and configured for retaining the compressible valve 200 within the internal cavity 133 of the assembled needleless connector 100. In operation, the internal sealing edge 122 may be arranged to provide blocking of fluid flow in conjunction with a primary seal portion 222 of the compressible valve 200.

According to various aspects of the present disclosure, the base portion 160 may have a top section 165 and a bottom section 167 located distally to the top section 165. In some embodiments, the top section 165 may include a valve seal support 250. The valve seal support 250 may include, but not limited to, a ramp surface 255 for engaging and radially supporting an inner surface 235 of the valve at the valve body portion 220. In some embodiments, the top section 165 of the base portion 160 may include a head 270 and a stem 275 longitudinally extending from the head 270. The head 270 may terminate in the ramp surface 255 which may engage the inner surface 235, and so the head 270 may radially support the inner surface 235 of the compressible valve 200. Accordingly, the housing 110 may be assembled with the compressible valve 200 such that in the assembled configuration, the head 270 including the ramp surface 255 may exert a force on the inner surface 235 of the compressible valve 200 to provide a radial support to the compressible valve 200. The radial support provided by the head 270 may advantageously prevent the compressible valve 200 from being "crushed in" or otherwise similarly deformed when the compressible valve member 200 is subject to high or otherwise excessive back pressures.

In accordance with various embodiments of the present disclosure, the top section 165 may further include a radially-outward extending ledge 265 for blocking, abutting and/or otherwise preventing the compressible valve 200 from being displaced into the inlet port 112 when subject to excessive back pressures. In particular, in some embodiments, the radially-outward extending ledge 265 may comprise a part of the head 270 of the top section 165 which is disposed distally to the ramp surface 255. As illustrated, the radially-outward extending ledge 265 may extend radially-outward from or transverse to a proximal end of the stem 275. The housing 110 may be assembled with the compressible valve 200 such that in the assembled configuration, the radially-outward extending ledge 265 may abut a corresponding structure of the compressible valve 200 to advantageously support and prevent the compressible valve 200 from being displaced proximally into the first port under excessive back pressures. In some embodiments, the bottom end portion 167 of the housing 110 may define the outlet port 123, which forms a second fluid passage to the internal cavity 133.

According to various embodiments of the present disclosure, the compressible valve 200 may have an asymmetrical geometry. For example, the compressible valve may be an asymmetrically-shaped valve 200 with a geometry which is not symmetrical for example about the longitudinal axis X of the housing 110. In these embodiments, the portion of the valve 200 to the left of the longitudinal axis X may not match the portion of the valve 200 to the right of the longitudinal axis X in shape or geometry.

According to various embodiments of the present disclosure, the asymmetrically-shaped compressible valve 200 may include a head portion 220, and a valve body portion 225 extending distally from the head portion 220. In some embodiments, as depicted, the head portion may be an elongate head portion. However, the various embodiments of the present disclosure are not limited to the aforementioned configuration. For example, in some embodiments, the head portion 220 may not in the shape or form of an elongate head. As depicted, the asymmetrically-shaped compressible valve 200 may further include a wall 230 having an inner surface 235 forming or otherwise defining a valve cavity 245.

In certain embodiments, the wall 230 of the asymmetrically-shaped compressible valve 200 may have a disproportionate cross-sectional thickness at different locations around its perimeter, as depicted in FIG. 1A. For example, in some embodiments, the wall 230 may have a cross-sectional thickness on opposing sides that differ by 50% or more. For example, a thicker side of the wall 230 may have 50% or more thickness than that of the opposing side. Although the relationship between the different thicknesses is described in terms of opposing sides, the sides do not need to be in direct opposition of each other and may be in other arrangements. In some embodiments, the thickness of the wall 230 may vary by greater than 75%, but less than 100%. For example, a thicker side of the wall 230 may have a thickness that is 75% to less than 100% greater than that of the opposing side. In some embodiments, the thickness of the wall 230 may vary by 100% or more. For example, a thicker side of the wall 230 may have a thickness that is 100% or more than that of the opposing side. In some embodiments, the wall 230 thickness may vary along its length such that it gradually increases in thickness from top to bottom along the narrowest wall thickness portion. In some embodiments, the wall 230 thickness may vary along its length such that it gradually decreases in thickness from top to bottom along the thickest wall thickness portion. The aforementioned configuration of the asymmetric valve geometry and wall 230 may allow a more controlled activation reliability in collapse of the compressible valve member.

In certain embodiments, the elongate head portion 220 may comprise a greater portion of the total length of the compressible valve 200 as compared with the valve body portion 225. For example, in some embodiments, the elongate head portion 220 may comprise greater than 50% of the total length of the compressible valve 200. In other embodiments, the elongate head portion 220 may comprise greater than 50% but less than 75% of the total length of the compressible valve 200. In yet other embodiments, the elongate head portion 220 may comprise greater than 75% but less than 100% of the elongate head portion 220. The aforementioned configuration of the asymmetrically-shaped compressible valve 200 with an elongate valve head portion 220 and asymmetric valve geometry advantageously allows the asymmetrically-shaped compressible valve 200 to be activated and retracted in a more controlled manner, as compared to the valves of currently existing needleless valves. Advantageously, the aforementioned configuration with elongate valve head portion 220 and asymmetric valve geometry may allow a more controlled activation and retraction of the compressible valve member, thereby preventing fluid from exiting (e.g., splashing off) the connector 100 upon a rapid disconnection of the medical implement (e.g., syringe) from the inlet or access port 112.

In contrast, due to the nature of currently existing and/or prior art needleless valve geometries, fluid is commonly deposited on the face of the valve head upon removal of the medical implement (e.g., a mating male luer or a syringe) used to apply an axial force to place the valve in an open position. In these currently existing needleless valves, fluid deposited on the valve head will occasionally separate from the valve and flow into the fluid path for administering to a patient, thereby causing anxiety along with potential blood stream diseases.

In accordance with various embodiments of the present disclosure, the elongate head portion 220 may include a top section 212 defining a first or secondary seal portion 214 of the compressible valve 200 on an outer surface thereof. The body portion 225 may further define a second or primary seal portion 222 at a proximal end of the body portion 225 and on the outer surface of the compressible valve 200. The primary seal portion 222 may be configured to engage against the inner surface 130 of the housing body portion 115 to form a primary seal therebetween. Similarly, the secondary seal portion 214 may be configured to engage against the inner surface 130 of the housing body portion 115 to form a secondary seal therebetween. Accordingly, the primary seal portion 222 may be configured to engage against the sealing edge 122 (positioned between the input port 112 and the top section 165 of the base portion 160) the to form the primary seal.

As depicted, the primary seal portion 222 may be spaced apart from and disposed distally to the secondary seal portion 214. In some embodiments, the primary seal portion 222 may be located adjacent to the base portion 160 or closer to the base portion 160 of the housing 110 than to the secondary seal portion 214. In particular, in some embodiments, the primary seal portion 222 may be located adjacent to the top section 165 or closer to top section 165 of base portion 160 of the housing 110 than to the secondary seal portion 214. Accordingly, a distance between the primary seal portion 222 and the top section 165 of base portion 160 may be smaller than a distance between the secondary seal portion 214 and the primary seal portion 222.

The aforementioned configuration locating the primary seal portion 222 of the compressible valve 200 close/adjacent to the top section 165 of base portion 160 as described above may advantageously create a more robust seal. Advantageously, the preload on the compressible valve 200 may remain more consistent with varying manufacturing tolerances of the needleless connector 100. In contrast, in currently existing connectors in which the valve has a primary seal located further from the base, the primary seal may lose preload due to buckling of the thin-walled valve over the longer distance between the primary seal and the base. For the same reason, the valve preload/sealing ability is sensitive to manufacturing tolerances.

According to various aspects of the present disclosure, as briefly described above, the compressible valve 200 may have a wall 230 including the inner surface 235 that defines valve cavity 245. As depicted, the compressible valve 200 may be coupled with and inside the housing 110 such that least a portion of the base portion 160 is disposed in the valve cavity 245. In particular, in some embodiments, the top section 165 of base portion 160 may be disposed in the valve cavity 245. Accordingly, in the assembled state of the housing 110 and the compressible valve member, the compressible valve 200 may be coupled with the housing 110 such that the inner surface 235 of the compressible valve 200 at the valve body portion 225 is seated and radially supported on and/or by the valve seal support 250. For example, in the assembled state, the ramp surface 255 may engage the inner surface 235 and so the head 270 may radially support the inner surface 235 of the compressible valve 200. Accordingly, the housing 110 may be assembled with the compressible valve 200 such that in the assembled configuration, the head 270 including the ramp surface 255 may exert a force on the inner surface 235 of the compressible valve 200 to provide a radial support to the compressible valve 200. The radial support provided by the head 270 may advantageously prevent the compressible valve 200 from being "crushed in" or otherwise similarly deformed when the compressible valve member 200 is subject to high or otherwise excessive back pressures.

In accordance with some embodiments of the present disclosure, wall 230 of the asymmetrically-shaped compressible valve 200 may define a radially-inward extending ledge 260. As depicted, the radially-inward extending ledge 260 may extend radially inward from the outer surface of the body portion 225 of the asymmetrically-shaped compressible valve 200. Accordingly, in the assembled state of the housing 110 and the compressible valve member 200, the radially-outward extending ledge 265 of the top section 165 of base portion 160 may abut the radially-inward extending ledge 260 of the asymmetrically-shaped compressible valve 200 to prevent the asymmetrically-shaped compressible valve 200 from being displaced into the first port. Accordingly, the radially-outward extending ledge 265 and the radially-inward extending ledge 260 may be formed with corresponding or complementary shapes, profiles, and/or geometries that allow the radially-outward extending ledge 265 to contact and abut the radially-inward extending ledge 260 to advantageously support and prevent the compressible valve 200 from being displaced proximally into the first port when subject to excessive back pressures.

As depicted, in some embodiments, radially-inward extending ledge 260 may be located adjacent to the primary seal portion 222. In particular, in some embodiments, the radially-inward extending ledge 260 can be located closer to the primary seal portion 222 than to the top section 165 of base portion 160. Accordingly, a distance between the radially-inward extending ledge 260 and the top section 165 of base portion 160 may be greater than a distance between the radially-inward extending ledge 260 and the primary seal portion 222. In some embodiments, adjacent positioning of the primary seal portion 222 and the radially-inward extending ledge 260 can provide a greater force of the compressible valve 200 against the internal sealing edge 122 at location of the primary seal portion 222 than if the primary seal portion 222 is positioned more remotely from the radially-inward extending ledge 260.

In some embodiments, the valve cavity may include an upper valve cavity and a lower valve cavity. In these embodiments, the radially-inward extending ledge 260 may be disposed between the upper and lower valve cavities. Furthermore, the head 270 of the base portion 160 may be disposed in the upper valve cavity, and the stem 275 may be disposed in the lower valve cavity.

According to various embodiments of the present disclosure, the compressible valve 200 may include any of the various materials used for producing mechanical valves for needleless connectors and other medical implements. In some implementations, the head portion 220 may include an elastomeric material, such as but not limited to, a silicone compound. Moreover, the primary seal portion 222 may include an elastomeric material. In some embodiments, all or some of the compressible valve 200 may be formed of liquid silicone rubbers.

Accordingly, the needleless connectors of the various embodiments described herein present several advantages over currently existing needleless connectors. For example, various embodiments of the present disclosure are generally directed to a self-sealing, needleless connector that incorporates a resilient, compressible valve disposed within a housing of the connector, in which the compressible valve has an asymmetric valve geometry with a long valve stem and a primary seal that is located close to the base side of the connector. The long valve stem and asymmetric valve geometry allow the valve to be activated and retracted in a more controlled manner. This prevents fluid from exiting (splashing off) the connector upon a rapid syringe disconnect.

As described herein, and as shall be appreciated, locating the primary seal of the valve close to the base of the connector housing creates a more robust seal. Advantageously, the preload on the valve remains more consistent with varying manufacturing tolerances of the connector. In contrast, in currently existing connectors in which the valve has a primary seal located far from the base, the seal may lose preload on the seal due to buckling of the thin-walled valve over a long distance. For the same reason, the valve preload/sealing ability is sensitive to manufacturing tolerances.

Further advantageously, due to the design of the long neck asymmetric valve geometry, the valve may activate and retract in a far more controlled manner than the valve in currently existing needleless connectors. In contrast, the currently existing needleless connectors present several challenges. For example, since the top half of the valve is solid silicone, the valve has a very high spring rate. As the valve of the currently existing needleless connectors is retracted quickly (such as during pulling off the syringe rapidly), the solid silicone portion of the valve tends to unwind and spring back violently. This may disadvantageously cause fluid to splash out of the currently existing connector. Additionally, the valve of the currently existing needleless connectors is very sensitive to manufacturing variances. Since the primary seal of the currently existing valve is supported by a long column of thin-walled silicone, the loss of preload on the valve becomes more pronounced with slight tolerance changes of the components or the assembly of the connector itself. Further, because the strength of the currently existing valve is dictated by the silicone, under high back pressures, the currently existing valve has a tendency to bulge out of the access port of the currently existing connector.

Furthermore, the base of the connector housing may advantageously be designed to support the primary seal of the valve in several ways. For example, in some embodiments at least a portion of the base may be designed to provide a radial support to the valve in the primary seal area. This radial support may advantageously prevent the valve from being "crushed in" or otherwise similarly deformed with high back pressures. In some embodiments, at least a portion of the base of the connector may be designed to "hold" the valve and prevent the valve from bulging out of the access port with high back pressures.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector comprising:

a housing comprising a central longitudinal axis, a housing body portion, and a base portion, wherein:

the housing body portion comprises an inner surface forming an internal cavity, and a first port forming a first fluid passage to the internal cavity; and the base portion comprises a top section including a valve seal support, the top section comprising a head and a stem longitudinally extending from the head, and a bottom section including a second port forming a second fluid passage to the internal cavity; and an asymmetrically-shaped valve disposed in the internal cavity and comprising a head portion, a flange portion, a valve body portion extending from the head portion to the flange portion, and a wall having an inner surface forming a valve cavity, the wall comprising a disproportionate cross-sectional thickness at different locations around its perimeter forming an asymmetric shape of the cavity when the head portion is positioned in the first port to obstruct the first fluid passage, wherein the valve cavity comprises an upper valve cavity and a lower valve cavity, and the asymmetrically-shaped valve is coupled with the housing such that the flange is coupled to the top section, the inner surface of the asymmetrically-shaped valve at the valve body portion is seated and radially supported on the valve seal support, the head of the base portion is disposed in the upper valve cavity and the stem of the base portion is disposed in the lower valve cavity, and a primary seal portion is formed by an outer surface of the valve body portion.

2. The needleless connector of claim 1, wherein the valve is coupled with the housing such that the top section of the base portion is disposed in the valve cavity with the inner surface of the valve at the valve body portion being seated and radially supported on the valve seal support.

3. The needleless connector of claim 1, wherein an outer surface of the head portion of the valve forms a secondary seal portion, and wherein the primary seal portion is spaced apart from the secondary seal portion.

4. The needleless connector of claim 3, wherein the primary seal portion is configured to engage against the inner surface of the housing body portion to form a primary seal therebetween, and the secondary seal portion is configured to engage against the inner surface of the housing body portion to form a secondary seal therebetween.

5. The needleless connector of claim 4, wherein the inner surface of the housing body portion comprises a sealing edge between the first port and the top section of the base portion, the primary seal portion configured to engage against the sealing edge to form the primary seal.

6. The needleless connector of claim 3, wherein the primary seal portion is located closer to the base portion of the housing than to the secondary seal portion such that a distance between the primary seal portion and the base portion is smaller than a distance between the secondary seal portion and the primary seal portion.

7. A needleless connector comprising:

a housing comprising a central longitudinal axis, a housing body portion, and a base portion, wherein:

the housing body portion comprises an inner surface forming an internal cavity, and a first port forming a first fluid passage to the internal cavity; and the base portion comprises a top section including a valve seal support, the top section comprising a head and a stem longitudinally extending from the head, and a bottom section including a second port forming a second fluid passage to the internal cavity; and an asymmetrically-shaped valve disposed in the internal cavity and comprising an elongate head portion, a flange portion, a valve body portion extending from the elongate head portion to the flange portion, and a wall having an inner surface forming a valve cavity comprising an upper valve cavity and a lower valve cavity, the wall comprising a disproportionate cross-sectional thickness at different locations around its perimeter and forming an asymmetric shape of the cavity when the head portion is positioned in the first port to obstruct the first fluid passage, wherein the wall defines a radially-inward extending ledge disposed between the upper and lower valve cavities with the head positioned in the upper valve cavity and the stem positioned in the lower valve cavity, the top section further comprises a radially-outward extending ledge which abuts the radially-inward extending ledge of the of the valve to prevent the valve from being displaced into the first port, and an outer surface of the valve body portion forms a primary seal portion configured to engage against the inner surface of the housing body portion to form a primary seal therebetween.

8. The needleless connector of claim 7, wherein a longitudinal extent of the elongate head portion comprises a first length and a longitudinal extent of the valve body portion comprises a second length, the first length being greater than the second length.

9. The needleless connector of claim 7, wherein the valve is coupled with the housing such that the top section of the base portion is disposed in the valve cavity with the inner surface of the valve at the asymmetrically-shaped valve body portion being seated and radially supported on the valve seal support.

10. The needleless connector of claim 7, wherein an outer surface of the elongate head portion of the valve forms a secondary seal portion, and wherein the primary seal portion is spaced apart from the secondary seal portion.

11. The needleless connector of claim 10, wherein the secondary seal portion is configured to engage against the inner surface of the housing body portion to form a secondary seal therebetween.

12. The needleless connector of claim 11, wherein the inner surface of the housing body portion comprises a sealing edge between the first port and the top section of the base portion, the primary seal portion configured to engage against the sealing edge to form the primary seal.

13. A needleless connector comprising:

a housing comprising a central longitudinal axis, a housing body portion, and a base portion, wherein:

the housing body portion comprises an inner surface forming an internal cavity, and a first port forming a first fluid passage to the internal cavity; and the base portion comprises a top section comprising a head and a stem longitudinally extending from the head, and a bottom section including a second port forming a second fluid passage to the internal cavity; and an asymmetrically-shaped valve disposed in the internal cavity and comprising an elongate head portion, a flange portion, a valve body portion extending from the elongate head portion to the flange portion, and a wall having an inner surface forming a valve cavity comprising an upper valve cavity and a lower valve cavity, the wall comprising a disproportionate cross-sectional thickness at different locations around its perimeter forming having an asymmetric shape of the cavity when the head portion is positioned in the first port to obstruct the first fluid passage, wherein the head of the base portion is positioned in the upper valve cavity, and the stem of the base portion is positioned in the lower valve cavity;

wherein: an outer surface of the valve body portion comprises a primary seal portion, and an outer surface of the elongate head portion comprises a secondary seal portion spaced apart from the primary seal portion; and the primary seal portion is located adjacent the base portion of the housing such that a distance between the primary seal portion and the base portion is smaller than a distance between the secondary seal portion and the primary seal portion.

14. The needleless connector of claim 13, wherein a longitudinal extent of the elongate head portion comprises a first length and a longitudinal extent of the valve body portion comprises a second length, the first length being greater than the second length.

15. The needleless connector of claim 13, wherein the primary seal portion is configured to engage against the inner surface of the housing body portion to form a primary seal therebetween, and the secondary seal portion is configured to engage against the inner surface of the housing body portion to form a secondary seal therebetween.

16. The needleless connector of claim 15, wherein the inner surface of the housing body portion comprises a sealing edge between the first port and a top section of the base portion, the primary seal portion configured to engage against the sealing edge to form the primary seal.

17. The needleless connector of claim 13, wherein the wall defines a radially-inward extending ledge disposed between the upper valve cavity and the lower valve cavity, and the top section comprises a radially-outward extending ledge, the radially-outward extending ledge abutting the radially-inward extending ledge of the of the valve to prevent the valve from being displaced into the first port.

* * * * *